US006391850B2

(12) United States Patent
Bouck et al.

(10) Patent No.: US 6,391,850 B2
(45) Date of Patent: May 21, 2002

(54) METHODS AND COMPOSITIONS FOR INHIBITING ANGIOGENESIS

(75) Inventors: Noel P. Bouck, Oak Park; David W. Dawson; Paul R. Gillis, both of Chicago, all of IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 09/875,223

(22) Filed: Jun. 6, 2001

Related U.S. Application Data

(60) Division of application No. 09/122,079, filed on Jul. 23, 1998, now Pat. No. 6,288,024, which is a continuation-in-part of application No. 08/899,304, filed on Jul. 23, 1997, now abandoned.

(51) Int. Cl.[7] .................................... A61K 38/16

(52) U.S. Cl. ..................... 514/2; 514/21; 424/574; 424/537; 424/571; 434/70.1; 434/70.3

(58) Field of Search .................. 514/2, 21; 424/537, 424/571, 574; 435/70.1, 70.3

(56) References Cited

U.S. PATENT DOCUMENTS 4,996,159 A 2/1991 Glaser .................... 435/70.5

FOREIGN PATENT DOCUMENTS

WO WO93/24529 12/1993
WO WO95/33480 12/1995

OTHER PUBLICATIONS

Alberdi and Becerra, Invest. Ophthalmol. Vis. Sci., 37, S791 (1996) (abstract #3642).
Alberdi et al., Biochemistry, 37, 10643–10652 (1998).
Araki et al., J. Neurosci. Res., 53, 7–15 (1998).
Bain et al., Gene Therapy, 1, S68.
Barany et al., J. Peptide Protein Res., 30, 705–739 (1987).
Becerra, "Structure–Function Studies on PEDF" Chapter 21 in Chemistry and Biology of Serpins, Church et al., eds. (Plenum Press, 1997).
Becerra et al., J. Biol. Chem., 268, 23148–23156 (1993).
Becerra et al., J. Biol. Chem., 270, 25992–99 (1995).
Berns and Giraud, Annals NY Acad. Sci., 772, 95–104 (1995).
Casey and Li, Am. J. Ophthalmol., 124, 521–529 (1997).
Chader et al., Invest. Ophthalmol. Vis. Sci., 37, S791 (1996) (abstract #3641).
DiPaolo et al., Exp. Cell Res., 220, 173–185 (1995).
Doggett et al., Mech. Ageing Dev., 65, 239–255 (1992).
Feher et al., Invest. Ophthalmol. Vis. Sci., 38, S591 (1997) (abstract #2753).
Fink et al., Annu. Rev. Neurosci., 19, 265–287 (1996).
Folkman et al., "Tumor Angiogenesis", Chapter 10, pp.206–232 in The Molecular Basis of Cancer, Mendelsohn et al., eds. (WB Saunders, 1995).
Folkman, Cancer Res., 46, 467–73 (1986).
Folkman, J. Nat. Cancer Inst., 82,4–6 (1989).
Folkman and Klagsbrun, Science, 235, 442–47 (1987).
Folkman and Shing, J. Biol Chem., 267 (16), 10931–34 (1989).
Gasparini, Eur. J. Cancer, 32A (14), 2379–85 (1996).
Gastl et al., Oncology, 54, 177–184 (1997).
Goliath et al., Molecular Vision, 2:5 (1996).
Jiang et al., J. Invest. Dermatol., 104, 523–25 (1995).
Kozaki et al., J. Biol. Chem., 273, 15125–15130 (1998).
Kyritsis et al., Exp. Eye Res., 38, 411–421 (1984).
Merrifield, J. Am. Chem. Soc., 85, 2149–2154 (1963).
O'Reilly et al, Cell 88, 277–85 (1997).
O'Reilly et al., Cell 79, 315–28 (1994).
Ortego et al., Invest. Ophthalmol. Vis. Sci., 37, 2759–2767 (1996).
Palmieri et al., Proc. Am. Assoc. Cancer Res., 38, 587 (1997) (abstract #3940).
Paus et al., Lab Invest. 71, 134–40 (1994).
Paus et al., Lab Invest. 60, 365–69 (1989).
Perez–Mediavilla et al., Biochim. Biophys. Acta, 1398, 203–214 (1998).
Phillips et al., Cancer Res., 56, 606–611 (1996).
Pignolo et al, J. Biol. Chem., 268, 8949–8957 (1993).
Pignolo et al., J. Cell. Physiol., 162, 110–118 (1995).
Potempa et al., J. Biol. Chem., 269, 15957–15960 (1994).
Rakmilevich et al., PNAS, 93, 6291–96 (1996).
Rubin, Nature Med., 2, 632–633 (1996).
Shirozu et al., Genomics, 37, 273–280 (1996).
Singh et al., Invest. Ophthalmol. Vis. Sci., 38, S591 (1997) (abstract #2752).
Singh et al., Mol. Vis., 4, 7 (1998).
Slavc et al., Int. J. Cancer, 72, 277–282 (1997).
Slominski et al., J. Invest. Dermatol., 102, 862–69 (1994).
Steele et al., PNAS, 90(4), 1526–30 (1993).
Stratikos et al., Protein Sci., 5, 2575–2582 (1996).
Sugita et al., J. Neurosci. Res.,49, 710–18 (1997).
Taniwaki et al., J. Neurochem., 64, 2509–2517 (1995).
Taniwaki et al., J. Neurochem., 68,26–32 (1997).
Teicher et al, Int. J. Cancer, 57, 920–25 (1994).
Tombran–Tink et al., Exp. Eye Res., 53, 411–14 (1991).
Tombran–Tink et al., Genomics, 19, 266–272 (1994).

(List continued on next page.)

*Primary Examiner*—Jean C. Witz
(74) *Attorney, Agent, or Firm*—Morgan, Lewis & Bockius, LLP

(57) ABSTRACT

The present invention provides a method of inhibiting angiogenesis within a tissue by providing exogenous SLED to cells associated with the tissue. The presence of exogenous SLED inhibits angiogenesis within the tissue, in part by interfering with the ability of vascular endothelia to expand within the tissue. The invention also provides a method for determining the severity of a tumor be assaying for the presence of SLED within the tumor. To facilitate the inventive methods, the present invention provides pharmaceutical compositions including sources of SLED.

3 Claims, 7 Drawing Sheets

OTHER PUBLICATIONS

Tombran–Tink and Johnson, Invest. Ophthalmol. Vis. Sci., 30, 1700–1707 (1989).

Tombran–Tink et al., J. Comp. Neurol., 317, 175–186 (1992).

Tombran–Tink et al., J. Neurosci., 15, 4992–5003 (1995).

Tombran–Tink et al., Mol. Vis., 2, 11 (1996).

Tresini et al., Cancer Res., 58, 1–4 (1998).

Weidner, New Eng. J. Med., 324(1), 1–8 (1991).

Wu and Becerra, Invest. Ophthalmol. Vis. Sci., 37, 1984–1993 (1996).

Wu et al., Protein Expression and Purification, 6, 447–456 (1995).

Xu et al., Cancer Res., 51, 4481–4485 (1991).

Zetter, Annu. Rev. Med., 49, 407–424 (1998).

METHODS AND COMPOSITIONS FOR INHIBITING ANGIOGENESIS

CROSS-REFERENCE TO RELATED APPLICATIONS

This application is a divisional of U.S. application Ser. No. 09/122,079, filed on Jul. 23, 1998 now U.S. Pat. No. 6,288,024, which is a continuation-in-part of U.S. application Ser. No. 08/899,304, filed on Jul. 23, 1997, now abandoned.

STATEMENT REGARDING FEDERALLY SPONSORED RESEARCH AND DEVELOPMENT

This invention was made with Government support under Grant Number CA52750 and CA64239 awarded by the National Institutes of Health. The United States Government may have certain rights in this invention.

BACKGROUND OF THE INVENTION

Angiogenesis is the fundamental process by which new blood vessels are formed. The process involves the migration of vascular endothelial cells into tissue, followed by the condensation of such endothelial cells into vessels. Angiogenesis may be induced by an angiogenic agent or be the result of a natural condition. The process is essential to a variety of normal body activities, such as reproduction, development and wound repair. Although the process is not completely understood, it involves a complex interplay of molecules that stimulate and molecules that inhibit the growth and migration of endothelial cells, the primary cells of the capillary blood vessels. Under normal conditions, these molecules appear to maintain the microvasculature in a quiescent state (i.e., without capillary growth) for prolonged periods which can last for several years or even decades. The turnover time for an endothelial cell is about 1,000 days. Under appropriate conditions, however (e.g., during wound repair), these same cells can undergo rapid proliferation and turnover within a much shorter period, and five days is typical under these circumstances. (Folkman and Shing, *J. Biol. Chem.,* 267(16), 10931–34 (1989); Folkman and Klagsbrun, *Science,* 235, 442–47 (1987)).

Although angiogenesis is a highly regulated process under normal conditions, many diseases (characterized as "angiogenic diseases") are driven by persistent unregulated angiogenesis. In such disease state, unregulated angiogenesis can either cause a particular disease directly or exacerbate an existing pathological condition. For example, ocular neovascularization has been implicated as the most common cause of blindness and underlies the pathology of approximately 20 eye diseases. In certain previously existing conditions such as arthritis, newly formed capillary blood vessels invade the joints and destroy cartilage. In diabetes, new capillaries formed in the retina invade the vitreous humor, causing bleeding and blindness.

Both the growth and metastasis of solid tumors are also angiogenesis-dependent (Folkman, *J. Cancer Res.,* 46, 467–73 (1986); Folkman, *J. Nat. Cancer Inst.,* 82, 4–6 (1989); Folkman et al., "Tumor Angiogenesis," Chapter 10, pp. 206–32, in *The Molecular Basis of Cancer,* Mendelsohn et al., eds. (W. B. Saunders, 1995)). It has been shown, for example, that tumors which enlarge to greater than 2 mm. in diameter must obtain their own blood supply and do so by inducing the growth of new capillary blood vessels. After these new blood vessels become embedded in the tumor, they provide nutrients and growth factors essential for tumor growth as well as a means for tumor cells to enter the circulation and metastasize to distant sites, such as liver, lung or bone (Weidner, *New Eng. J. Med.,* 324(1), 1–8 (1991)). When used as drugs in tumor-bearing animals, natural inhibitors of angiogenesis can prevent the growth of small tumors (O'Reilly et al., O'Reilly et al., *Cell,* 79, 315–28 (1994)). Indeed, in some protocols, the application of such inhibitors leads to tumor regression and dormancy even after cessation of treatment (O'Reilly et al., *Cell,* 88, 277–85 (1997)). Moreover, supplying inhibitors of angiogenesis to certain tumors can potentiate their response to other therapeutic regimens (e.g., chemotherapy) (see, e.g., Teischer et al., *Int. J. Cancer,* 57, 920–25 (1994)).

Although several angiogenesis inhibitors are currently under development for use in treating angiogenic diseases (Gasparini, *Eur. J. Cancer,* 32A(14), 2379–85 (1996)), there are disadvantages associated with several of these proposed inhibitory compounds. For example, suramin is a potent angiogenesis inhibitor, but, at doses required to reach antitumor activity, causes severe systemic toxicity in humans. Other compounds, such as retinoids, interferons and antiestrogens appear safe for human use but have only a weak anti-angiogenic effect. Still other compounds may be difficult or costly to make. In view of these problems, there exists a need for methods and compositions for inhibiting angiogenesis.

BRIEF SUMMARY OF THE INVENTION

The present invention provides a method of inhibiting angiogenesis within a tissue by providing exogenous SLED (an antiangiogenic protein) to endothelial cells associated with the tissue. The presence of exogenous SLED will inhibit angiogenesis within the tissue, in part by interfering with the ability of vascular endothelia to expand within the tissue. The invention also provides a method for determining the prognosis of a tumor by assaying for the presence of SLED within the tumor. To facilitate the inventive method, the present invention provides pharmaceutical compositions including sources of SLED.

The methods and compositions of the present invention are clinically useful for treating a host of diseases associated with angiogenesis, and for interfering with angiogenesis associated with reproductive functions. The methods and compositions are also diagnostically useful for assessing the prognosis of tumors and other disorders associated with angiogenesis. Furthermore, the methods and compositions are useful reagents for investigation of angiogenesis in the laboratory setting. These and other advantages of the present invention, as well as additional inventive features, will be apparent from the accompanying drawings and in the following detailed description.

BRIEF DESCRIPTION OF THE DRAWINGS

FIG. 2A depicts data concerning WI-38 cells. FIG. 2B depicts data concerning human foreskin fibroblasts. FIG. 2C depicts data concerning vascular smooth muscle cells. FIG. 2D depicts data concerning neutrophils.

DETAILED DESCRIPTION OF THE INVENTION

Figure 1:
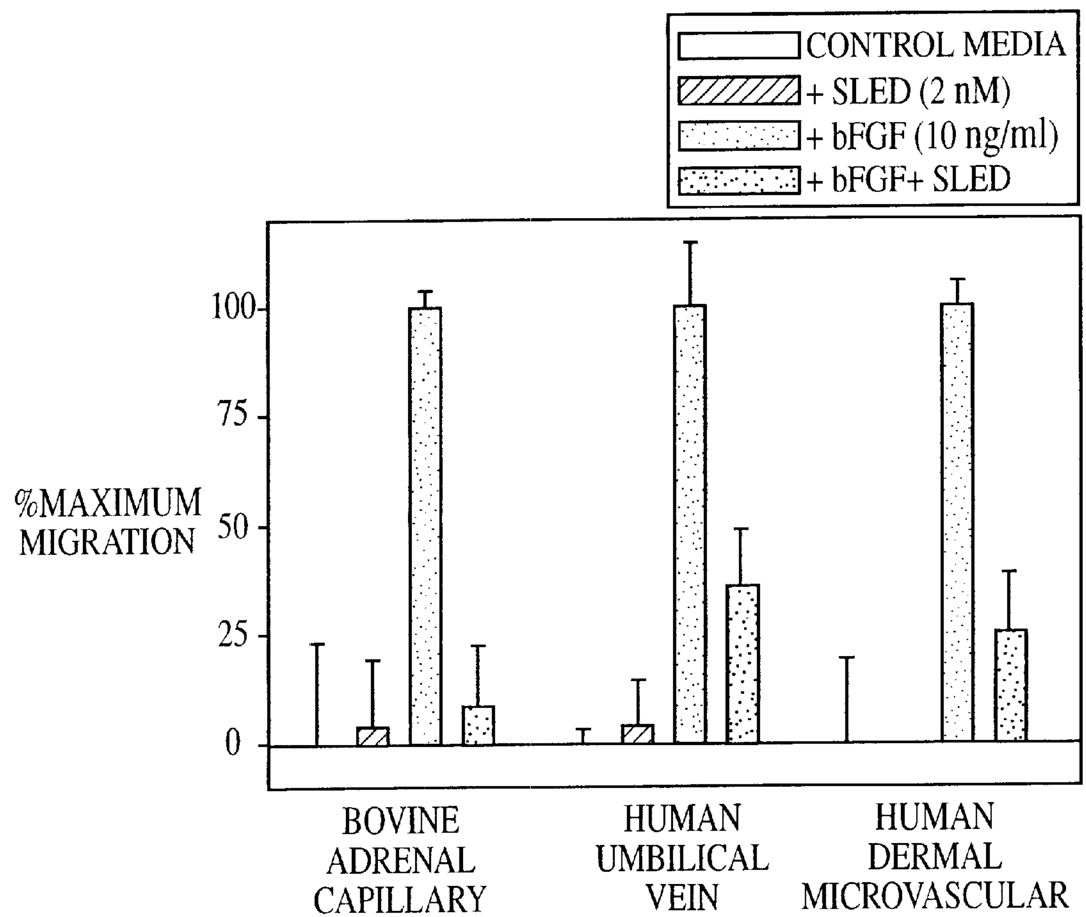
FIG. 1 graphically illustrates the ability of SLED to inhibit the migration of endothelial cells.
Figure 2A:
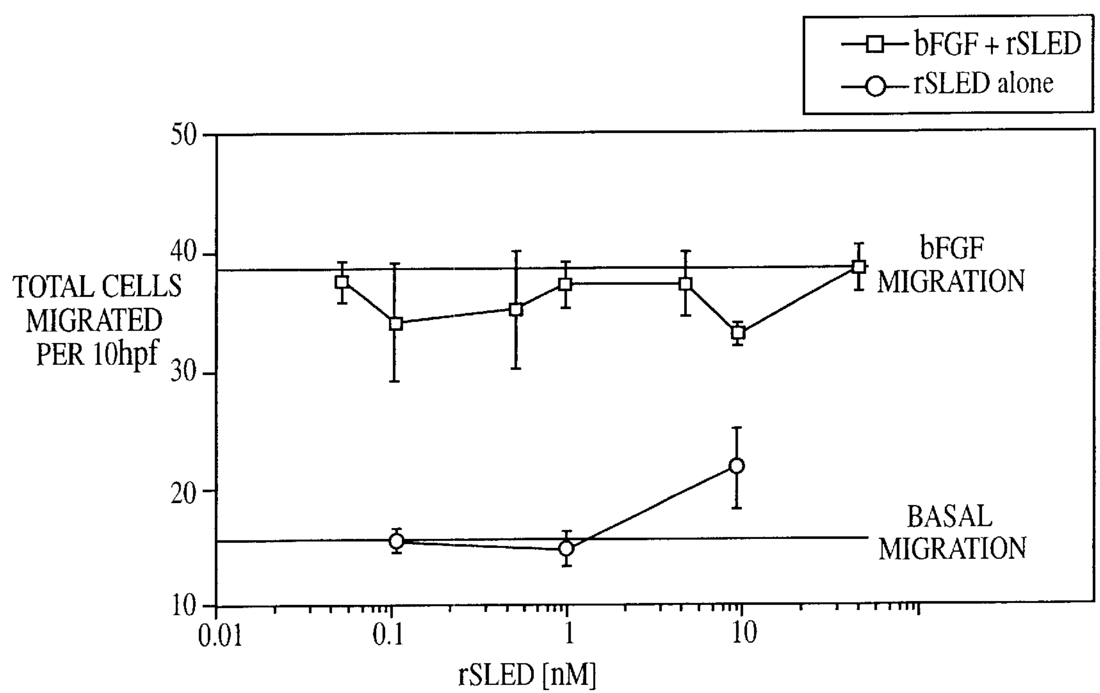
FIGS. 2A–2D demonstrates the specificity of SLED for vascular endothelia by graphically representing the inability of various doses of SLED to inhibit the migration of cells other than vascular endothelial cells.
Figure 2B:
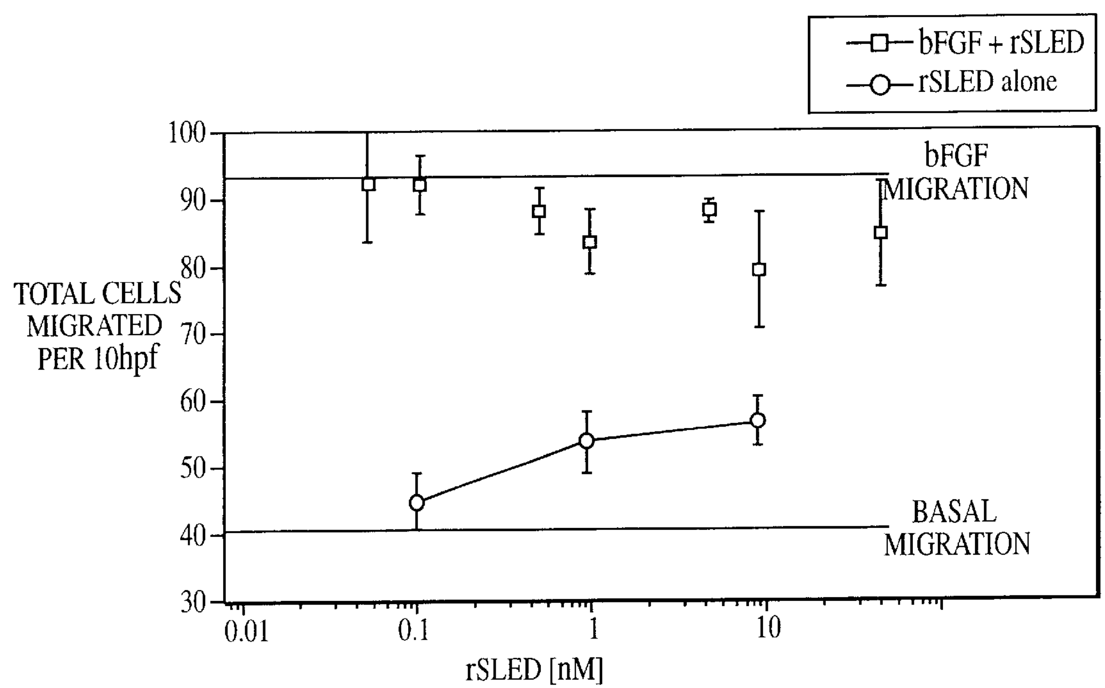
Figure 2C:
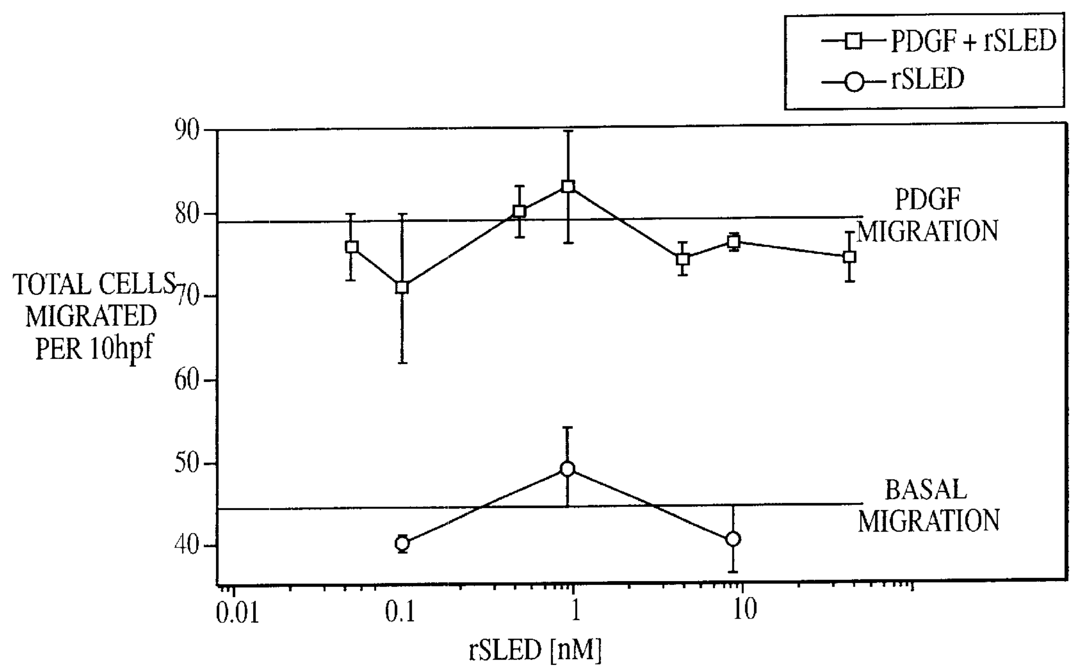
Figure 2D:
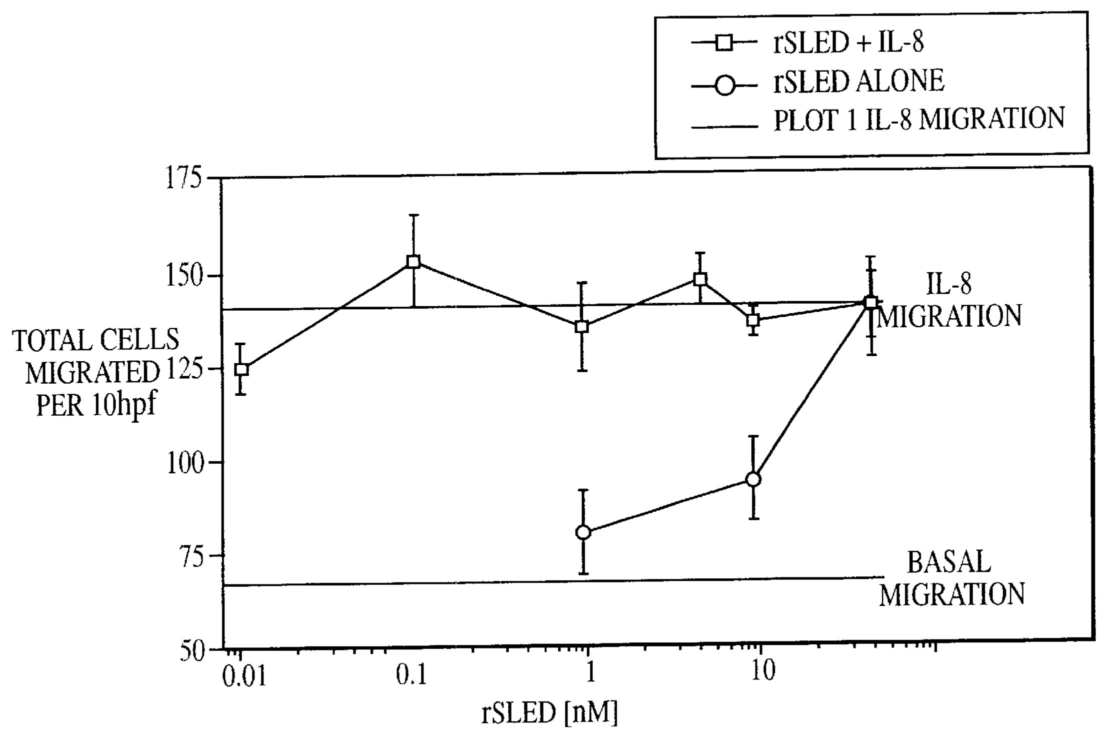

Within the context of the inventive method, SLED is a protein having potent antiangiogenic properties, and it includes any antiangiogenic derivative of pigment epithelium derived factor (PEDF, Steele et al., *Proc. Nat. Acad. Sci.* (USA), 90(4), 1526–30 (1993)), such as those described herein. One form of SLED polypeptide (Full length PEDF) is set forth at SEQ ID NO:1; however, the invention is not limited to the use of this exemplary sequence. Indeed, other PEDF sequences are known in the art (see, e.g., published international patent applications WO 95/33480 and WO 93/24529), and genetic sequences can vary between different species and individuals, and this natural scope of allelic variation is included within the scope of the invention. Additionally and alternatively, a SLED polypeptide can include one or more point mutations from the exemplary sequence or another naturally occurring SLED polypeptide. Thus, a SLED polypeptide is typically at least about 75% homologous to all or a portion of SEQ ID NO:1 and preferably is at least about 80% homologous to all or a portion of SEQ ID NO:1 (e.g., at least about 85% homologous to SEQ ID NO:1); more preferably the SLED polypeptide is at least about 90% homologous to all or a portion of SEQ ID NO:1 (such as at least about 95% homologous to all or a portion of SEQ ID NO:1), and most preferably the SLED polypeptide is at least about 97% homologous to all or a portion of SEQ ID NO:1. Indeed, the SLED polypeptide can also include other domains, such as epitope tags and His tags (e.g., the protein can be a fusion protein).

Within the context of the present invention, a SLED polypeptide can be or comprise insertion, deletion, or substitution mutants of a known PEDF sequence or derivative thereof. Preferably, any substitution is conservative in that it minimally disrupts the biochemical properties of the SLED polypeptide. Thus, where mutations are introduced to substitute amino acid residues, positively-charged residues (H, K, and R) preferably are substituted with positively-charged residues; negatively-charged residues (D and E) preferably are substituted with negatively-charged residues; neutral polar residues (C, G, N, Q, S, T, and Y) preferably are substituted with neutral polar residues; and neutral non-polar residues (A, F, I, L, M, P, V, and W) preferably are substituted with neutral non-polar residues. Moreover, the SLED polypeptide can be an active fragment of a known PEDF protein or fragment thereof. Indeed, it has been found that truncated fragments derived from SEQ ID NO:1 are active SLED polypeptides. For example, it is believed that residues 1 through 20 of SEQ ID NO:1 are cleaved during secretion and thus are dispensable for SLED activity. Moreover, other active SLED polypeptides comprise sequences derived from residues 21 through 382 of SEQ ID NO:1, such as residues 44 through 157 of SEQ ID NO:1 (e.g., residues 45 through 121 of SEQ ID NO:1). Of course, while insertion, deletion, or substitution mutations can affect glycosylation of the protein, a SLED polypeptide need not be glycosylated to possess the requisite antiangiogenic properties for use in the inventive method.

SLED polypeptides inhibit angiogenesis, in part, by attenuating the migration of endothelial cells, thus reducing the ability of endothelia to expand within the tissue. Thus, the invention provides a method of inhibiting endothelial cell migration by providing exogenous SLED to such cells. Aside from attenuating angiogenesis, the method is useful for treating disorders associated with stimulation of endothelial cell migration such as intestinal adhesions, Crohn's disease, atherosclerosis, scleroderma and hypertrophic scars (e.g., keloids).

In accordance with the inventive method, SLED is provided to endothelial cells associated with the tissue of interest. Such cells can be cells comprising the tissue of interest, exogenous cells introduced into the tissue, or neighboring cells not within the tissue. Thus, for example, the cells can be cells of the tissue, and SLED is provided to them in situ such that the SLED contacts the cells. Alternatively, the cells can be cells introduced into the tissue, in which case the SLED can be transferred to the cells before they are so introduced into the tissue (e.g., in vitro), as well as being transferred in situ after introduction into the tissue.

The tissue with which the endothelial cells are associated is any tissue in which it is desired to inhibit the migration or expansion of endothelia, (e.g., for inhibiting angiogenesis). In one application, the tissue can be eye tissue, in which case the presence of exogenous SLED will inhibit novel angiogenesis associated with a variety of disorders of the eye. For example, the inventive method is useful for treating eye injury, hypoxia, infection, surgery, laser surgery, diabeties, retinoblastoma or other diseases or disorders of the eye. In this respect, the method is useful for preventing blindness or retarding loss of vision associated with a variety of eye diseases.

In another application, the tissue is skin tissue, in which case the presence of exogenous SLED prevents neovascularization associated with several skin diseases. For example, the inventive method is useful for treating diseases and disorders such as psoriasis, scleroderma, tumors of the skin, neovascularization as a consequence of infection (e.g., cat scratch disease, bacterial ulceration, etc.) or other skin disorders. Where SLED is provided to the skin, it can be provided to the surface of the skin or to skin tissue beneath the skin's surface. Furthermore, transfer of SLED to skin of a mammal can also stimulate the growth of hair in the skin. Without being bound by any particular theory, it is believed that SLED affects hair growth by mediating angiogenesis within the hair follicle.

In other embodiments, the tissue is a tumor (e.g., a cancerous tumor), in which case the inventive method will inhibit the growth of blood vessels within and to the tumor. Inhibiting the growth of blood vessels within tumors prevents sufficient nutrients and oxygen from being supplied to the tumor to support growth beyond a given size. Thus, the inventive method can prevent the nucleation of tumors from cancerous cells already present due to genetic predisposition (e.g., BRCA-1 mutation carriers, Li Fraumeni patients with p53 mutations, etc.) or the presence of external carcinogens (e.g., tobacco, alcohol, industrial solvents, etc.). Aside from preventing tumerogenesis, the inventive method can retard the growth of existing tumors, thus rendering them more easily contained and excised. This application is highly advantageous for treating tumors that are difficult to operate on (e.g., brain or prostate tumors). Moreover, minimizing the number of blood vessels within existing tumors lessens the probability that the tumor will metastasize. In treating tumors, the method can be used alone or in conjunction with other treatments, to control the growth of tumors. Indeed, employing the inventive method can potentiate the response of some tumors to other therapies. For example, the inventive method optionally can be employed as a pretreatment for (e.g., for about a week in advance of), and continued during, a chemotherapeutic or radiation regimen.

Where the inventive method is applied to other tissues, the prevention of neovascularization effectively treats a host of disorders. Thus, for example, the inventive method can be used as part of a treatment for disorders of blood vessels (e.g., hemangiomas and capillary proliferation within atherosclerotic plaques), muscle diseases (e.g., myocardial angiogenesis or angiogenesis within smooth muscles), joints (e.g., arthritis, hemophiliac joints, etc.), and other disorders associated with angiogenesis (e.g., Osler-Webber Syndrome, plaque neovascularization, telangiectasia, angiofibroma, wound granularization, etc.).

Aside from treating disorders and symptoms associated with neovascularization, the inhibition of angiogenesis can be used to modulate or prevent the occurrence of normal physiological conditions associated with neovascularization. Thus, for example the inventive method can be used as a birth control. In accordance with the inventive method, the presence of SLED within the ovaries or endometrium can attenuate neovascularization associated with ovulation, implantation of an embryo, placenta formation, etc.

Within the context of the inventive method, SLED can be supplied alone or in conjunction with other known antiangiogenic factors. For example, SLED can be used in conjunction with antibodies and peptides that block integrin engagement, proteins and small molecules that inhibit metalloproteinases (e.g., marmistat), agents that block phosphorylation cascades within endothelial cells (e.g., herbamycin), dominant negative receptors for known inducers of angiogenesis, antibodies against inducers of angiogenesis or other compounds that block their activity (e.g., suramin), or other compounds (e.g., retinoids, IL-4, interferons, etc.) acting by other means. Indeed, as such factors modulate angiogenesis by different mechanisms, employing SLED in combination with other antiangiogenic agents can potentiate a more potent (and potentially synergistic) inhibition of angiogenesis within the desired tissue.

As discussed herein, SLED is a proteinatious factor. Thus, in one protocol, the method involves providing SLED by supplying a SLED polypeptide to the cells (e.g., within a suitable composition). Any suitable method can be employed to obtain a SLED polypeptide for use in the present invention. Many suitable SLED polypeptides can be purified from tissues which naturally produce SLED or from media conditioned by a variety of SLED-producing cells (e.g., retinoblastoma cell line WER127). For example, it is known that SLED is produced by all types of muscle, megakaryocytes of the spleen, fibroblasts, kidney tubules, cerebellar Purkinje cells, piliosebaceous glands of hair follicles, and retinal cells. A particularly good source of naturally occurring SLED is vitreous and aqueous humors extracted from the eye. One protocol for purifying SLED from protein extracts of these (or other sources) is by concentration/dialysis using a 30 kDa ultrafiltration membrane followed by protein precipitation in a range of about 65% to about 95% ammonium sulfate, followed by a lentil lectin sepharose column at 0.5 M methyl-α-D-mannopytanoside, followed by gradient/isocratic elution at 0.5M NaCl from a PHARMACIA HiTrap heparin column. Other protocols for purifying SLED polypeptides are known in the art (see, e.g., published international patent applications WO 95/33480 and WO 93/24529). The native SLED polypeptide represented by SEQ ID NO:1 is identified via SDS-PAGE as a protein of about 45 kDa. Other SLED polypeptides can be synthesized using standard direct peptide synthesizing techniques (e.g., as summarized in Bodanszky, *Principles of Peptide Synthesis* (Springer-Verlag, Heidelberg: 1984)), such as via solid-phase synthesis (see, e.g., Merrifield, *J. Am. Chem. Soc.,* 85, 2149–54 (1963); Barany et al., *Int. J. Peptide Protein Res.,* 30, 705–739 (1987); and U.S. Pat. No. 5,424,398). Of course, as genes for SLED polypeptides are known (see, e.g., published international patent applications WO 95/33480 and WO 93/24529); see also GenBanc accession no. U29953 SEQ ID NO:2)), or can be deduced from the polypeptide sequences discussed herein, a SLED polypeptide can be produced by standard recombinant methods.

In other protocols, SLED polypeptide can be provided to the tissue of interest by transferring an expression cassette including a nucleic acid disclosing SLED to cells associated with the tissue of interest. The cells produce and secrete the SLED polypeptide such that it is suitably provided to endothelial cells within the tissue to inhibit their migration and, thus, to attenuate angiogenesis within the tissue of interest. Coding sequences for SLED polypeptides are known (see, e.g., published international patent applications WO 95/33480 and WO 93/24529); see also GenBanc accession no. U29953 (SEQ ID NO:2)), and others can be deduced from the polypeptide sequences discussed herein. Thus, SLED expression cassettes typically employ coding sequences homologous to these known sequences, e.g., they will hybridize to at least a fragment of the known sequences under at least mild stringency conditions, more preferably under moderate stringency conditions, most preferably under high stringency conditions (employing the definitions of mild, moderate, and high stringency as set forth in Sambrook et al., *Molecular Cloning: A Laboratory Manual,* 2d edition, Cold Spring Harbor Press (1989)).

In addition to the SLED coding sequence, an expression cassette includes a promoter, and, in the context of the present invention, the promoter must be able to drive the expression of the SLED gene within the cells. Many viral promoters are appropriate for use in such an expression cassette (e.g., retroviral ITRs, LTRs, immediate early viral promoters (IEp) (such as herpesvirus IEp (e.g., ICP4-IEp and ICP0-IEp) and cytomegalovirus (CMV) IEp), and other viral promoters (e.g., late viral promoters, latency-active promoters (LAPs), Rous Sarcoma Virus (RSV) promoters, and Murine Leukemia Virus (MLV) promoters)). Other suitable promoters are eukaryotic promoters, such as enhancers (e.g., the rabbit β-globin regulatory elements), constitutively active promoters (e.g., the β-actin promoter, etc.), signal specific promoters (e.g., inducible and/or repressible promoters, such as a promoter responsive to TNF or RU486, the metallothionine promoter, etc.), and tumor-specific promoters.

Within the expression cassette, the SLED gene and the promoter are operably linked such that the promoter is able to drive the expression of the SLED gene. As long as this operable linkage is maintained, the expression cassette can include more than one gene, such as multiple genes separated by ribosome entry sites. Furthermore, the expression cassette can optionally include other elements, such as polyadenylation sequences, transcriptional regulatory elements (e.g., enhancers, silencers, etc.), or other sequences.

The expression cassette must be introduced into the cells in a manner suitable for them to express the SLED gene contained therein. Any suitable vector can be so employed, many of which are known in the art. Examples of such vectors include naked DNA vectors (such as oligonucleotides or plasmids), viral vectors such as adeno-associated viral vectors (Bems et al., *Ann. N.Y Acad. Sci.,* 772, 95–104 (1995)), adenoviral vectors (Bain et al., *Gene Therapy,* 1, S68 (1994)), herpesvirus vectors (Fink et al., *Ann. Rev. Neurosci.,* 19, 265–87(1996)), packaged amplicons (Federoff et al., *Proc. Nat. Acad. Sci.* USA, 89, 1636–40 (1992)), pappiloma virus vectors, picornavirus vectors, polyoma virus vectors, retroviral vectors, SV40 viral vectors, vaccinia virus vectors, and other vectors. In addition to the expression cassette of interest, the vector can also include other genetic elements, such as, for example, genes encoding a selectable marker (e.g., β-gal or a marker conferring resistance to a toxin), a pharmacologically active protein, a transcription factor, or other biologically active substance.

Once a given type of vector is selected, its genome must be manipulated for use as a background vector, after which it must be engineered to incorporate exogenous polynucleotides. Methods for manipulating the genomes of vectors are well known in the art (see, e.g., Sambrook et al., supra) and include direct cloning, site specific recombination using recombinases, homologous recombination, and other suitable methods of constructing a recombinant vector. In this manner, the expression cassette can be inserted into any desirable position of the vector.

The vector harboring the SLED expression cassette is introduced into the cells by any means appropriate for the vector employed. Many such methods are well-known in the art (Sambrook et al., supra; see also Watson et al., *Recombinant DNA,* Chapter 12, 2d edition, Scientific American Books (1992)). Thus, plasmids are transferred by methods such as calcium phosphate precipitation, electroporation, liposome-mediated transfection, gene gun, microinjection, viral capsid-mediated transfer, polybrene-mediated transfer, protoplast fusion, etc. Viral vectors are best transferred into the cells by infecting them; however, the mode of infection can vary depending on the virus.

Cells into which the SLED gene has been transferred can be used in the inventive method as transient transformants. Alternatively, where the cells are cells in vitro, they can be subjected to several rounds of clonal selection (if the vector also contains a gene encoding a selectable marker, such as a gene conferring resistance to a toxin) to select for stable transformants.

Within the cells, the SLED gene is expressed such that the cells express and secrete the SLED polypeptide. Successful expression of the gene can be assessed via standard molecular biological techniques (e.g., Northern hybridization, Western blotting, immunoprecipitation, enzyme immunoassay, etc.). Reagents for detecting the expression of SLED genes and the secretion of SLED from transfected cells are known in the art (see, e.g., published international patent applications WO 95/33480 and WO 93/24529); Steele et al., supra).

Depending on the location of the tissue of interest, SLED can be supplied in any manner suitable to provide it to endothelial cells within the tissue of interest. Thus, for example, a composition containing a source of SLED (i.e., a SLED polypeptide or a SLED expression cassette, as described herein) can be introduced into the systemic circulation, which will distribute the source of SLED to the tissue of interest. Alternatively, a composition containing a source of SLED can be applied topically to the tissue of interest (e.g., injected as a bolus within a tumor or intercutaneous or subcutaneous site, applied to all or a portion of the surface of the skin, dropped onto the surface of the eye, etc.).

Where the source of SLED is a SLED polypeptide (e.g., within a suitable composition), it is provided in a concentration and for a time sufficient to inhibit angiogenesis within the tissue. Where SLED is produced naturally, it can be present in concentrations as high as about 250 nM. Because SLED is non-toxic, it can be supplied to tissues in a far more concentrated form. However, given SLED's potency, it can be employed in the inventive method at far reduced concentrations, such as about 50 nM or less (e.g., about 10 nM or less). Indeed, in some protocols, about 2 nM SLED or less effectively inhibits angiogenesis and endothelial cell migration. Depending on the formulation of a composition comprising the protein, it is supplied over a time course sufficient to retard angiogenesis within the desired tissue. In some protocols (e.g., where the SLED is supplied to the surface of skin or to the eye), repeated application enhances the antiangiogenic effect and may be required in some applications. Where the source of SLED is a SLED expression cassette, the cells expressing the cassette produce an effective amount of the protein (i.e., sufficient to inhibit angiogenesis in the tissue).

To facilitate the inventive method, the invention provides a pharmacological composition comprising a source of SLED and a suitable diluent. In addition to the source of SLED, the composition includes a diluent, which includes one or more pharmacologically-acceptable carriers. Pharmaceutical compositions for use in accordance with the present invention can be formulated in a conventional manner using one or more pharmacologically or physiologically acceptable carriers comprising excipients, as well as optional auxiliaries which facilitate processing of the active compounds into preparations which can be used pharmaceutically. Proper formulation is dependent upon the route of administration chosen. Thus, for systemic injection, the source of SLED can be formulated in aqueous solutions, preferably in physiologically compatible buffers. For transmucosal administration, penetrants appropriate to the barrier to be permeated are used in the formulation. Such penetrants are generally known in the art. For oral administration, the source of SLED can be combined with carriers suitable for inclusion into tablets, pills, dragees, capsules, liquids, gels, syrups, slurries, diposomes, suspensions and the like. For administration by inhalation, the source of SLED is conveniently delivered in the form of an aerosol spray presentation from pressurized packs or a nebuliser, with the use of a suitable propellant. The source of SLED can be formulated for parenteral administration by injection, e.g., by bolus injection or continuous infusion. Such compositions can take such forms as suspensions, solutions or emulsions in oily or aqueous vehicles, and can contain formulatory agents such as suspending, stabilizing and/or dispersing agents. For application to the skin, the source of SLED can be formulated into a suitable gel, magma, creme, ointment, or other carrier. For application to the eyes, the source of SLED can be formulated in aqueous solutions, preferably in physiologically compatible buffers. The source of SLED can also be formulated into other pharmaceutical compositions such as those known in the art.

Because it is known that SLED is absent from some tumors, the invention also provides a method for determining the prognosis of a tumor by assaying for the presence of SLED within the tumor. The method involves obtaining tissue or fluid from the tumor and detecting the presence or absence of SLED within the tissue or fluid. Greater the SLED concentration within the tumor correlates with a lesser likelihood that the tumor is undergoing angiogenesis. Thus, higher SLED concentration within the tumor is indicative of a relatively early stage of tumerogenesis and is, thus, an optimistic indication. Conversely, the absence of SLED within a given tumor is indicative of a more advanced stage of tumerogenesis. The method can employ an assay for the presence of PEDF gene expression (e.g., via rtPCR, Northern hybridization, in situ hybridization etc.). Alternatively, the method can employ an assay for the presence of secreted SLED (e.g., immunological assays, SLED purification and PAGE analysis, etc.). Reagents for detecting the presence of SLED within such tumors are known in the art (see, e.g., published international patent applications WO 95/33480 and WO 93/24529).

While it is believed that one of skill in the art is fully able to practice the invention after reading the foregoing detailed description, the following examples further illustrate some of its features. As these examples are included for purely illustrative purposes, they should not be construed to limit the scope of the invention in any respect.

The procedures employed in these examples, such as cell culture, manipulation of protein and DNA, etc. are well known in the art (see generally Sambrook et al., *Molecular Cloning, A Laboratory Manual,* Cold Spring Harbor Laboratory, Cold Spring Harbor, N.Y. (1989)). Accordingly, in the interest of brevity, the experimental protocols are not discussed in detail.

EXAMPLE 1

This example demonstrates that SLED prevents endothelial cell migration.

The migration of different vascular endothelial cell types was determined by adding SLED to cultured endothelial cells. Specifically, endothelial cells isolated from bovine adrenal capillaries, human umbilical chords, and human dermal microvascular tissue.

The cells were plated on gelatinized Nucleopore membranes (5 μm pores for bovine capillary cells and 8 μm pores for other cells) in an inverted modified Boyden chamber. After two hours, the chamber was reinverted and test substances added to the top wells of each. Specifically, populations were exposed to either culture medium alone (control), 10 ng/ml bFGF, 2 nM SLED (full length PEDF), or both 10 ng/ml bFGF (Fibroblast Growth Factor) and 10 nM SLED. The cells were then permitted to migrate for 3–4 hours. Following this, the membranes were fixed and stained, and the number of cells that had migrated were counted.

The results of the assay are presented in FIG. 1 as a percentage of maximal migration (error bars represent standard error measurement, n=4). As is depicted, all three types of vascular endothelial cells exhibited nearly 100% migration in the presence of bFGF. However, in the presence of SLED, considerably less migration was observed. These results demonstrate that SLED inhibits endothelial cell migration. These results are surprising, given that the PEDF protein is known to induce neural differentiation of cultured retinoblastoma tumor cells, to be a neurotrophic factor for cerebellar granular cells and a cytostatic factor for glial cells (Taniwaki et al., *J. Neurochem.,* 68, 26–32 (1997); Sugita et al., *J. Neurosci. Res.,* 49, 710–18 (1997); Tombran-Tink et al., *Exp. Eye Res.,* 53, 411–14 (1991); Becerra, "Structure-Function Studies on PEDF," Chapter 21, in *Chemistry and Biology of Serpins,* Church et al., eds. (Plenum Press, 1997)).

EXAMPLE 2

This example demonstrates that the prevention of cell migration by SLED is specific for endothelial cells.

The ability of SLED to prevent migration of fibroblasts or smooth muscle was tested using cells obtained from human diploid fibroblast cell line WI-38, human foreskin fibroblasts, vascular smooth muscle, and normal human neutrophils.

The assay was performed as indicated in Example 1, except that the dose of SLED varied from 0.01 nM to about 50 nM and that the migration assay was performed without inverting the chambers. Moreover, the inducer of migration varied with the cell type (IL-8 was used at 1 μg/ml and PDGF was used at 250 pg/ml).

The results of this experiment are presented in FIGS. 2A–2D. As indicated in these figures, SLED did not inhibit migration of any of the cell lines. This result indicates that the antimigratory activity of SLED is specific for vascular endothelial cells.

EXAMPLE 3

This example demonstrates that SLED is among the most potent inhibitors of endothelial cell migration.

Using a protocol similar to that outlined in Example 1, bovine adrenal capillary endothelial cells were exposed to bFGF, SLED, and several known antiangiogenic factors. The amount of a given factor necessary to achieve 50% of migration was determined and is reported here as $ED_{50}$. A smaller $ED_{50}$ measurement indicates a more potent antiangiogenic factor. The results of this experiment, presented in Table 1, indicate that SLED is a highly potent antiangiogenic factor.

TABLE 1

| Agent | $ED_{50}$ (nM) |
|---|---|
| SLED | 0.1–0.5 |
| Thrombospondin | 0.5 |
| Endostatin | 3.0 |
| Angiostatin | 3.5 |
| Retinoic Acid | 15 |
| Tissue Inhibitor of Metalloproteinase-1 | 3500 |
| Captopril | 10,000 |

EXAMPLE 4

This example demonstrates that SLED inhibits the angiogenic activity of known angiogenic agents.

Using a protocol similar to that outlined in Example 1, bovine adrenal capillary endothelial cells were exposed to five known angiogenic agents alone or in combination with 0.1 μg/ml SLED. In particular, aFGF was employed at a concentration of 50 ng/ml, bFGF was employed at a concentration of 10 ng/ml, IL-8 was employed at a concentration of 40 ng/ml, PDGF was employed at a concentration of 250 pg/ml, and VEGF was employed at a concentration of 100 pg/ml.

Figure 3:
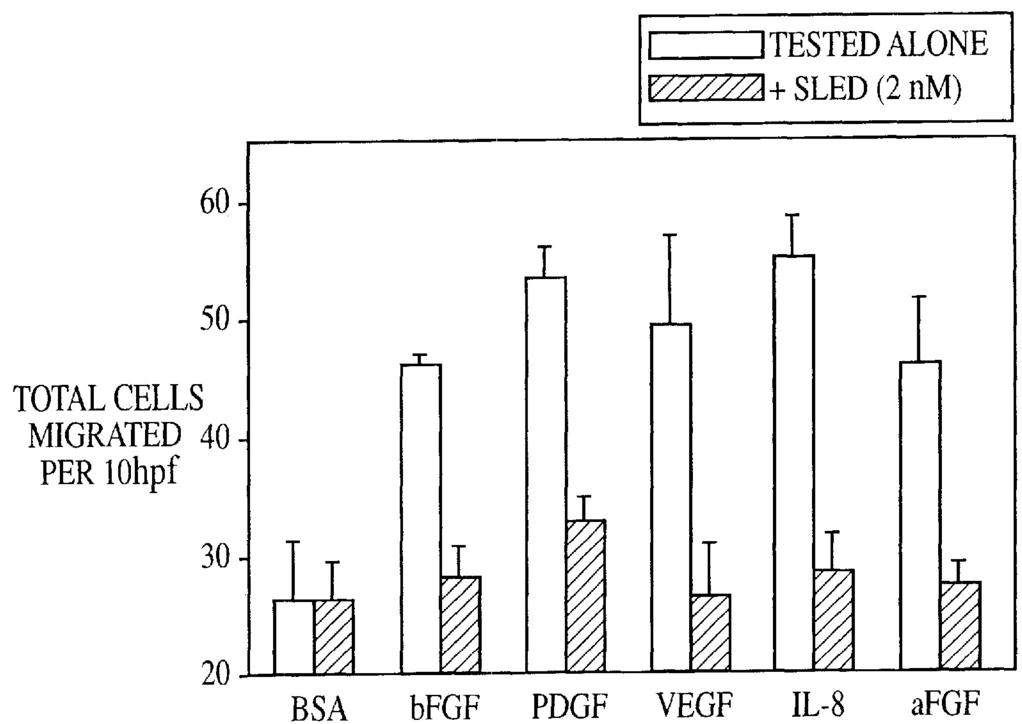
FIG. 3 is a dose-response curve representing the antiangiogenic activity of one type of SLED polypeptide (full length PEDF).

The results of the assay are presented in FIG. 3. As is depicted, the migration of the cells was considerably inhibited by SLED, regardless of the angiogenic agent. These results demonstrate that SLED-mediated inhibition of vascular endothelial migration is not specific for bFGF induction, but that SLED acts generally to inhibit migration of these cells.

EXAMPLE 5

This example demonstrates that SLED inhibits neovascularization in vivo.

Pellets containing various proteins were implanted in the avascular corneas of rats. Pellets either contained or lacked bFGF, and the pellets also contained either SLED or bovine serum albumin (BSA) as a control. After seven days, the corneas of the rats were examined to note whether angiogenesis had occurred.

The results of this assay are presented in Table 2. As indicated, no vascularization was observed from injecting pellets lacking bFGF. However, vascularization was observed in all eyes implanted with bFGF and BSA. Co-injection of bFGF and SLEF, however, resulted in no neovascularization in any cornea. These results indicate that SLED is a potent inhibitor of angiogenesis in vivo.

TABLE 2*

| Treatment | Without bFGF | With bFGF |
|---|---|---|
| SLED (8 nM) | 0/3 | 0/3 |
| BSA | 0/2 | 4/4 |

*results expressed as number of corneas with angiogenesis/number of test animals.

EXAMPLE 6

This example demonstrates that SLED polypeptides other than the full PEDF protein are active antiangiogenic agents.

Trypsin digestion of the complete PEDF protein cleaves the protein at amino acid 352 of SEQ ID NO:1, removing the approximately 3–5 kDa carboxy-terminal portion of the protein (Becerra et al., *J. Biol. Chem.,* 270, 25992–99 (1995)). This procedure was employed to generate the fragments, and the truncated N-PEDF fragment (representing amino acids 21–382 of SEQ ID NO:1) was purified from trypsin by heparin affinity chromatography.

Figure 4:
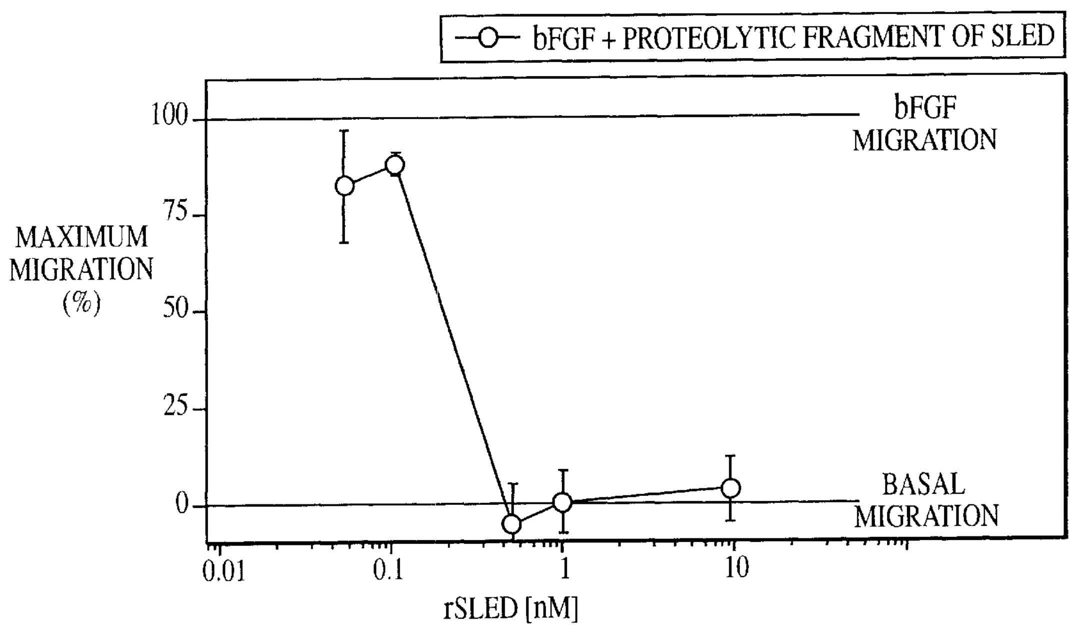
FIG. 4 is a dose response curve representing the antiangiogenic activity of one type of SLED polypeptide (a fragment of PEDF).

Using a protocol similar to that outlined above, various concentrations of either full length PEDF or the truncated peptide were assayed for their respective abilities to affect endothelial cell migration. Data generated for the truncated peptide are indicated in FIG. 4. Comparison of these data with the activity of the full length PEDF (see FIG. 3) reveals both proteins to be similarly potent at inhibiting endothelial cell migration. These results indicate that peptides other than full length PEDF are active SLED polypeptides.

EXAMPLE 7

This example demonstrates that exogenous SLED applied to the skin promotes the growth of hair therein.

In this example, the ability of SLED to induce hair growth is investigated using an established mouse model. In particular, in the C57BL/6 mouse strain, a change in skin pigmentation correlates with the physiology of the skin being in anagen (growing), catagen (transitional), or telogen (resting) phase (see, e.g., Jiang et al., *J. Invest. Dermatol.,* 104, 523–25 (1995); Slominski et al., *J. Invest. Dermatol.,* 102, 862–69 (1994); Paus et al., *Lab. Invest.,* 71, 134–40 (1994); and Paus et al., *Lab. Invest.,* 60, 365–69 (1989)). Six or seven week old C57BL/6 mice have pink skin, indicating telogen phase. Depilation of these mice triggers hair growth and skin darkening.

To test for the effect of SLED on hair growth, six or seven-week-old C57BL/6 mice are inspected for the absence of skin pigmentation to verify that their skin is in telogen (resting) stage. Following this, they are anesthetized and their hair is removed by clipping (rather than shaving) so as not to trigger anagen. A plasmid having a SLED expression cassette is precipitated onto gold particles. Similarly, a control plasmid having a β-galactosidase expression cassette is also precipitated onto gold particles. To avoid significant trauma to the skin (which could trigger anagen), the plasmids are transferred to the prepared skin of the mice at 250 psi using a gene gun (see, e.g., Rakmilevich et al., *Proc. Nat. Acad. Sci.* (USA), 93, 6291–96 (1996)).

At weekly intervals following gene transfer, animals are sacrificed and the presence of circulating levels of administered gene product are assessed by Western blotting. Additionally, skin from the prepared and transfected skin is assayed for the presence of gene product within the skin by immunohistochemistry. The mice are also visually observed weekly for the presence of coloration within the treated areas of skin.

Results indicate that transfer of the β-galactosidase or SLED expression cassette leads to detectable product in the animals. However, skin transfected with the β-gal expression cassette does not progress to anagen any more rapidly than untreated skin. Conversely, skin treated with the SLED expression cassette becomes pigmented more rapidly than untreated skin. The results indicate that transfer of exogenous SLED to the skin promotes the growth of hair.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method for stimulating the growth of hair in a mammal, said method comprising providing exogenous SLED to cells associated with the skin of said mammal under conditions sufficient for said SLED to stimulate the growth of hair in said mammal.

2. The method of claim 1, wherein said SLED is supplied to said cells via the systemic circulation.

3. The method of claim 1, wherein said SLED is supplied to said cells via topical administration.

* * * * *

```
                         SEQUENCE LISTING

<160> NUMBER OF SEQ ID NOS: 2

<210> SEQ ID NO 1
<211> LENGTH: 362
<212> TYPE: PRT
<213> ORGANISM: Homo sapiens

<400> SEQUENCE: 1

Met Gln Ala Leu Val Leu Leu Leu Cys Ile Gly Ala Leu Leu Gly His
  1               5                  10                  15
```

-continued

```
Ser Ser Cys Gln Asn Pro Ala Ser Pro Pro Glu Glu Gly Ser Pro Asp
            20                  25                  30

Pro Asp Ser Thr Gly Ala Leu Val Glu Glu Glu Asp Pro Phe Phe Lys
        35                  40                  45

Val Pro Val Asn Lys Leu Ala Ala Ala Val Ser Asn Phe Gly Tyr Asp
    50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
            100                 105                 110

Ile Ser Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
    210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
        275                 280                 285

Ile Glu Glu Ser Leu Thr Ser Glu Phe Ile His Asp Ile Asp Arg Glu
    290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Gly Gly Thr Pro Gly Trp Leu
        355                 360
```

<210> SEQ ID NO 2
<211> LENGTH: 22484
<212> TYPE: DNA
<213> ORGANISM: Homo sapiens
<220> FEATURE:
<221> NAME/KEY: Unsure
<222> LOCATION: 1...22484
<223> OTHER INFORMATION: "n" means either a, c, t, or g

<400> SEQUENCE: 2

```
gcggccgcag ggtggactgt gctgaggaac cctgggccca gcaggggtgg cagcccgcgc     60
```

-continued

```
agtgccacgt ttggcctctg gccgctcgcc aggcatcctc caccccgtgg tcccctctga    120
cctcgccagc cctcccccgg gacacctcca cgccagcctg gctctgctcc tggcttcttc    180
ttctctctat gcctcaggca gccggcaaca gggcggctca gaacagcgcc agcctcctgg    240
tttgggagaa gaactggcaa ttagggagtt tgtggagctt ctaattacac accagcccct    300
ctgccaggag ctggtgcccg ccagccgggg gcaggctgcc gggagtaccc agctccagct    360
ggagacagtc agtgcctgag gatttggggg aagcaggtgg ggaaaccttg gcacagggct    420
gacaccttcc tctgtgccag agcccaggag ctggggcagc gtgggtgacc atgtgggtgg    480
gcacgcttcc ctgctggggg tgcagggggt ccacgtggca gcggccacct ggagccctaa    540
tgtgcagcgg ttaagagcaa gcccctggaa gtcagagagg cctggcatgg agtcttgctt    600
cttgcaaacg agccgtgtgg agagagagat agtaaatcaa caaagggaaa tacatggtct    660
gtccgaggat gagctgccgg agagcaatgg tgaaagtgaa gtgggggagg gggcggggct    720
gggaggaaaa gccttgtgag aaggtgacac gagagcacgg ccttgaaggg gaagaaggag    780
ggcactatgg aggtcccggc gaagcgtggc ctggccgagg aacggcatgt gcagaggtcc    840
tgccgaggag ctcaagacaa gtaggggacg gtggggctgg agtggagaga gtgagtggga    900
ggaggagtag gagtcagaga ggagctcagg acagatcctt taggctctag ggacacgata    960
aacacagtgt tttttgtctt gtcaagtgtg tcctttttat ttttttgaaa gagtctcgct   1020
ctgtagccca ggctggagtg cagcggtgcg acctcggctc actgcaacct ctgcctcccg   1080
ggtccaagca attctcctgc ctcagcctcc cgagtagctg ggattacagg cacccgccac   1140
cacgcactgc taatttttgt attttagtag agaccgggtt ttgccatgtt ggtcaggctg   1200
gtctcgaact cctgacctca ggtgatccgc ccgcctcggc ctcccagagt ggtgtgagcc   1260
actatgccct gcagcacttg tcaagtcttt ctcagcgttc ccctcctctc cactgcagct   1320
cccagtgccc cagtctgggc ctcgtcttca cttcctggga tccctgacat tgcctgctag   1380
gctctccctg tctctggtct ggctgccttc actgtaacct ccacccagca ggtacctctt   1440
cagcacctcc catgaaccca gcagaatacc aagccctggg gatgcagcaa cgaacaggta   1500
gacgctgcac tccagcctgg gcgacagagc aagactccgc ctgaagaaaa aaaaaaggac   1560
caggccgggc gcggtggctc acgcctgtaa tcccagcact ttgggaggcc gaggtgggtg   1620
gatcatgagg tcaggagttc aagaccagcc tggccaaaat ggtgaaaccc cgtctctact   1680
gaaaaataca aaaattagct gggtgcagtg gcgggcgcct gtagtctcag ctactcagga   1740
ggctgaggca ggataattgc ttgaccccag gaggcagagg ttgcagtgaa ccgagatcac   1800
gccactgcac tccagcctgg gcgacagagc aagactctgc ctcaaaaaaa agaataaaaa   1860
taaaaaaaag gaccagatac agaaaacaga aggagacgta ctatgaagga aattggagag   1920
cttttgggat actgagtaac tcagggtggc ctttcccagg ggacatttag ctgagagata   1980
gacggtatga agacctgacc gttcagaaac aggggaagag gcagcagccc gggcaaaggc   2040
ctttggggca ggaaagggct tggatcactg gagaagcaga aagatggcca gtgtgaccag   2100
agtgtgacaa agtcagagaa aaccaggaag atggagctgg agacacaggc ggggccagat   2160
cacgagggtc ctcgcagacc agagcaaggg tttggatttt attccaagta tgaagggaag   2220
ctgctgaagt gtgttttcct ttacaatttg tagttgaaat ataatatgca aagtacacaa   2280
gtcttaacta tatgtaagct taatgaatgt ttccatgaac caaataccgc tgtgcaacca   2340
tcaccagctc aagagacgaa cccttctccc tcctcctgac tgccagtaac atagtggttc   2400
```

-continued

```
agctcaagaa acagaactct tctgacttcc cctaacatag cgggttttct tttttgtttt   2460
gtttttttgtt gttttttaag agacaatgtc tttattattt ttatttttttt ttatttttga   2520
gacggagtct tgctgtcgcc caggctggag tgcagtggtg cgatctcggc tcactgcagg   2580
ctctgccccc cggggttcat gccattctcc tgcctcagcc tccctagcag ctgggactac   2640
aggtgcccgc cacctcgccc ggctattttt ttgtattttt agtggagacg gggtttcacc   2700
gtgttagcca ggatggtctc gatctcctga cctcgtgatc cgcccacctc ggcctcccaa   2760
agtgctggga ttacaggcat gagccaccgc gcccagccaa gagacacggt cttgctctgt   2820
cgcccaggct ggatggagtg ccgtggtgcg atcacagctc gcggcagcct tgacatcctg   2880
ggctcaagca accttcctgc cttggcctcc caaatgttgg gattataggc atgagccact   2940
gtgcttggca tctattcatc tttaatgtca agcaggcaat tgaatatttg atcagggata   3000
gaattgtcta tttgggggta tgcagatgtg cttcatgtca tggaactggg ccgggcgcgg   3060
tggctcatgc ctataatccc agcactttgg gaggccgagg caggcggatc ataaggtcag   3120
gagatcgaga ccatccgggc caacacggtg aaaccccgtc tctactaaaa atacaaaaat   3180
taggcaggtg tggtggtgcg tgcctgtagt cccagctact cagggaggct gagacaggag   3240
aattgattga acctgggagg cagaggttgt agtgagccaa gatcgcgcca ctgcactcca   3300
gcctgggcga catgagcgag actccgtctc aaaaataaac aaaaaaaagt catggaattg   3360
atggaaattg cctaagggga gatgtagaag aaaagggtc tcaggatcaa gccagcagag   3420
aaggcagaaa aggtaaggtg tgtgaggtgg cagaaaaagg gaagagtgtg gacagtgagg   3480
gtttcaagga ggaggaactg tctactgcct cctgccaagg acggaggtgt ccactgccag   3540
ttgacataag gtcacccatg aacttggtga caggaatttc agtggagaag tggccacaga   3600
cacaagtcta gaattgaaat gggagccgag gcagcgtaga caaaagagga aactgctcct   3660
tccagagcgg ctctgagcga gcaccgagaa atgggcagtg gctttagggg atgtagcgtc   3720
aaggaagtgt cttttaaaga agtcgggggc cgggcacggt ggctcacgcc tgtagtccca   3780
gcactttggg aggccgaggc aggcagatca cttgaggtca ggagttcgag accagcctgg   3840
ctaacacgat gaaaccccgt ctctactaaa aatacaaaaa attagctggg cacggtggct   3900
cgtgcctgta atcccagcac tttgggaggc agaggtgggc agatcacttg aggtcaggag   3960
tttgagacca gcctagccaa catggtgaaa ccccatctct actaaaacta caaaaattag   4020
ccgggagtgg tggcacgtgc ctgtaatccc agccagtcag gaggctgagg caggagaatc   4080
actggaatcc tggaggtgga ggtggcagtg agccgagatg gtacctctgt actccagcct   4140
gggggacaga gtgagactcc gtctcaaaaa aaaaagaagg tggggaagga tctttgaggg   4200
ccggacacgc tgaccctgca ggagaggaca cattcttcta acaggggtcg gacaaaagag   4260
aactcttctg tataatttat gattttaaga tttttattta ttattatttt ttatagaggc   4320
aagcattttt caccacgtca cccaggctgg tctccaactc ctgggctcaa gtgtgctggg   4380
attatagcca tgagtcacca cacctggccc agaaacttta ctaaggactt atttaaatga   4440
tttgcttatt tgtgaatagg tattttgttc acgtggttca caactcaaaa gcaacaaaaa   4500
gcacccagtg aaaagccttc ctctcattct gatttccagt cactggattc tactcttggg   4560
atgcagtgtt tttcatctct tttttgtatc cttttggaaa tagtattctg ctttaaaaag   4620
caaatacagg ccaggtatgg tggctcactc ctgtaatccc agcactttgg gaggccgagg   4680
caggtgatca cctaaggtca ggagttcaag accagcctgg ccaatatggt gaaaccctgt   4740
ctgtaccaaa acacaaaaac aaaaacaaaa acaaaaatta gccgggcgtg gtggcgtgct   4800
```

-continued

```
cctgtaatcc cagctactca ggaggctgag gcaggagaat cgcttgaacc tgggaggcag   4860
aggttgcagt gagccgagat tgtgccactg tactccagcc tgggccacag agcaaggttc   4920
catctcaaac aaaacaaaac aaaacaaaca aaaaaacaaa acaaaagcta atacaaacac   4980
atatacaata gacaaaactg taaatatttt attattttta ttttttttag tagagacagg   5040
gtttcaccat gttggccagg atggtctcaa actcctgacc tcaggtgatc cacccacctc   5100
agcctcccga tagttaggat tacaggcatg agccaccaca cccggcctaa aattgtaaac   5160
gttttagaag aaagtataga tgaatccctt cgtgatctcg gggaagaaga gattttttaa   5220
aaaagatacc aaaagaagca caaattataa aagaaaagat tgaaaatgtt ggtgttaaaa   5280
ttaaaaactt gttttaaaac aagcttgtgt aacccatgac ccacaggctg catgtggccc   5340
agaaaagctt tgactgcagc ccaacacaaa ttcgtaaact ttcctaaaac attatgagat   5400
ttttttgag attttgtttt gttttgtttt ttgttttttt agctcattcg gtatcattaa   5460
tgttagcata ttttacgtgg ggcccaagac aattcttctt ccaatgtgtc tcaggggagc   5520
caaaagattg gacacccctg ccataaacat gaaaagacaa tggccgggca cggtggctca   5580
cgcctgtaat cccagcactt tgggaggctg aggggggcgg gatcacctga ggtcaggagt   5640
ttgagacaag cgtgaccaat gtggtgaaac cctgtctcta ctaaaaatac aaaaattagc   5700
cgggcatgct cgtgcacacc tatagtccca actactcagc agggtgaggc aggagaacct   5760
cttgaacccg ggaagcggag gttgcagtga gccgacattg cacccctgca ctccagcctg   5820
ggtgacagag tgagtctcca ctggaaaaaa aaaaaaaaga acagtgtgat acattgacct   5880
aaggtttaag aacatgcaaa ctgatactat atatcactta gggacaaaaa cttacatggt   5940
aaaagtaaaa agaaatgtac gaaaataata aaaatcaaat tcaagatggt ggttatggtg   6000
acgggaaaga actgaggcgg aaatataagg ttgtcactat attgagaaat ttttctatct   6060
ttttttcttt tttcttttttt tgagacgggg tctcgctctg tcgcccagga tggagtgcag   6120
tggtgtgatc tcagctcact gcaacctccg cctcccaggt ttaagtgatt ctcctgcctc   6180
agactcccaa gtagctggga ctacaggtgc gcgccaacac acctgggtaa ttttgtttgt   6240
atttttagta gagatggggt ttcaccgtgt tgactaggct ggtctcgaac tcctgacctc   6300
aggtgatccc ccggcctcgg tctcccaaag tgctgggata acaagcgtga gccactgcgc   6360
ccagctttgt ttgcattttt aggtgagatg gggtttcacc acgttggcca ggctggtctt   6420
gaactcctga cctcaggtga tgcacctgcc tcagtctccc aaagtgctgg attacaggcg   6480
ttagcccctg cgcccggccc ctgaaggaaa atctaaagga agaggaaggt gtgcaaatgt   6540
gtgcgcctta ggcgtaatgg atggtggtgc agcagtgggt taaagttaac acgagacagt   6600
gatgcaatca cagaatccaa attgagtgca ggtcgcttta agaaaggagt agctgtaatc   6660
tgaagcctgc tggacgctgg attagaaggc agcaaaaaaa gctctgtgct ggctggagcc   6720
ccctcagtgt gcaggcttag agggactagg ctgggtgtgg agctgcagcg tatccacagg   6780
taaagcagct ccctggctgc tctgatgcca gggacggcgg gagaggctcc cctgggctgg   6840
ggggacaggg gagaggcagg ggcactccag ggagcagaaa agaggggtgc aagggagagg   6900
aaatgcggag acagcagccc ctgcaatttg ggcaaaaggg tgagtggatg agagagggca   6960
gagggagctg gggggacaag gccgaaggcc aggacccagt gatccccaaa tcccactgca   7020
ccgacggaag aggctggaaa ggcttttgaa tgaagtgagt gggaaacagc ggaggggcgg   7080
tcatggggag gaaaggggag ctaagctgct gggtcgggtc tgagcagcac cccaagactg   7140
```

-continued

```
gagcccgagg caaggaggct cacgggagct gcttccacca agggcagtca ggaaggcggc   7200
cgccctgcag cccagccctg gcccctgctc cctcggctcc ctgctacttt ttcaaaatca   7260
gctggtgctg actgttaagg caatttccca gcaccaccaa accgctggcc tcggcgccct   7320
ggctgagggc tgggatggag gacagctggg tccttctagc cagcccccac ccactctctt   7380
tggctacatg agtcaaggct gggcgaccaa tgaggttgtg gcctccggca aacaatgacc   7440
actatttagg ccggcaggtg tatagggcgt gggggcccag ctgccagtgc tggagacaag   7500
ggctgtccga gatgaaccct ttctgctgcc tgccaagcca ctgggagggg taggtctcag   7560
caggattccc agaaaccccg cccctgtcca gcctaggccc cccacccggt gttagctaac   7620
ccaacgttag cccccaggtt ccgtggggtt ggggggcagg gagtcctatt cttggggctg   7680
ctgcttctgg ggtgtgggga agtgcaactc cacggcaccc tgggctgact cattcagctt   7740
ctaaagcttc aggaaacatt gtttggggct gggtcaccat gggtgggcca gagaggaccc   7800
ctcaatcccc tccggagagc caggggaggg ggaggtgccc ttccccatgc tatctccgag   7860
gcccactgcc atgtggctga aggctgtgcg gttctgggaa gagggggagg tggcggtgga   7920
ggctgtttgt ctcctaactg ggcttaatct gaaacacatg tattggcttg agttgatccg   7980
cctcacgtgg aggcaagatc acaaaagctt ctgtgtttct tgatgtgggc aattgtcaga   8040
aaataaggcc tgaccttggc ccagcaggga gggtatctac ctctccctga gccctccccc   8100
gcctgctagg acgagagcgg ggcttggata ctgccctttg gacaggatgg catcattgtc   8160
tgtggctgca gccagccagc ggtcgcctgc tcagcccatg agcaaccact gtggacaggg   8220
tattgcgtgt gtgctgaggg gcgtccatgc agacccccac gcttgccctc tcactgccct   8280
tgtagggttt tcaatcatct ctcctcttcc cttatccaga tggcttgaag tggaggattc   8340
agacttgccg ttaatactct gggtccctgt gtctagctcg ggccaccttt tggacccatg   8400
tcccttccct gccaggctcc ctcacctcac ctcagcctac ccacattgtg acaatcatct   8460
accacctgat ctggggtttg ggcttagatt ctgtaggcac caagactaaa gtcgctcctt   8520
caagtccatt tgaattgtga ctttagtttc cttaaatact atgccaggat aatggccagg   8580
gatggtggct cacgcctgta ctcctggcac tttgggatgc tggtggatca cctgagatca   8640
ggattccagg ccagcctggc caacacggtg aaaccccatc tctactaaaa cataaaaatt   8700
aaccaggtgt ggtggcgggc acctgtaatc ccagctactc aggagactga ggcaggagaa   8760
ttgcttgaac ccgggaggtg gaagttgcac tgagctgaga tcgcgccact gcactttagc   8820
ctgggcgaca agagtgaaac tctgtctcaa aaacaaaaaa aactatgccg ggatgagcct   8880
gtctcctccc ttaatttctt acttgggcca gaggaactag aactaacaac ttctcttcta   8940
gccttgcctc ctgtgtacct cactgaattt ttggtctcta ataaaccagt ctgcagaggc   9000
tcaggggagg caggctcctg gcagctgggt ggggctggcc ccagccgggt ggagaccagc   9060
tgtaggcctg gatggtggtg aggcctctgt cttgcactgc agaaagcttt tcctgttgtc   9120
tacacgaaag ttttctccct gcatgtcagg gcagccacgt gcaagagcag ctggctggga   9180
acgcagaggt ctgcggctcg aggcggggtt tagaaagaaa accaggctgc ttcctgctgc   9240
ccgtcctgcc ttaagctgag taaactcaaa ggcaatcttc tttcatgcct cacgatattg   9300
tccagtggat tatctgattt aatttgaagg acgagagcca acaatcacac aacgtcctcc   9360
caaattttct gatccacttt gttctgggaa gtcaaaaagt gcgtgtgctg tgtgggtgga   9420
tgtttgtgta tataaatgga taatgaagga tgatgtgttg ggggccaggg caggggagac   9480
aacgctgttc agattctaca tttttttttc cttttttttt tttttttgag atggagtctt   9540
```

-continued

```
gctctgttgc ccagcctgga gtgcagtggc gcgatctcag ctcactgcaa cctccacttc   9600
ctggattcaa gtgattctcc tgccttagcc tcccaagtag ctgggattac aggcatgcgc   9660
caccacaccc ggctaatttt tgtattttta gtagagatgg ggtttctcca tgttggccag   9720
gatggtctca aactcctgac ctcaggtgat ctacccgcct cggcctctca aagtgctggg   9780
attacaggtt tgagccactg cgcctggcct tttttttttt ttttgagatg gagttttcac   9840
tcttgttgcc caggctggag tgcagtggtg cgatcttggc tcactgcaac ctccacctcc   9900
caagttcaag tgattctcca gccttagccc tccaagtagc tgggactaca ggtgtgtgcc   9960
accatgcctg gctattttat tttattttat tttatttatt tatttttgag actaagtctt  10020
gctctgttgc ccaggctgga gtgcagtggc ataatcggct cactgcaacc tctgcctccc  10080
aggttcaagt gattctcctg cctcagcctc ctgagtaact gggattacag gggcctgcca  10140
ccacgcctgg ctacttttg tatttttagt atagatgggg tttcaccatg ttggccaggc  10200
tggtctcgaa ctcctgacct caggctatcc gcctgcctca gcctcccaaa gtgctgggat  10260
tacaggcatg agccactgtg ctcggtagtt gttttatttt aatagtaggt tattttattt  10320
ccattttaca agagaaaaaa tggtgattta aagagctact aagacacagc actgagacca  10380
tgtgtgatgg catgcgcctg cagtcccagc tactcacgag gctgaggcag gaggatcaca  10440
tgaggtcagg agttccaggc tgtggagtgc tatggttgtg tagtgaatag ccactacact  10500
ccagcctggg cagcacagca agatcttgtc tcccaaaaaa aaaaaaaaaa aaaaatttca  10560
aatgtgaacc caggatctct gaccctaggc cctgcactcc taaccatggg aggaagagct  10620
cttgaaaggg aactgtggga gaagggaatg agctgccttg tgaggccaca gaagtccaaa  10680
gacagcttga gaatttggag ggacagcacg tgccggactg ggtgcctcta tgcttggtat  10740
ccggtgattc catggaggag acctgggttc tgccccattc tcctgggagg ggttgcccaa  10800
agtcttatca ccggagtggg tcagctgcct ccaggacaaa gctttagcat acacttgtgc  10860
tgggccatac tccacgtgga gaagccctgc tggggctggg gccccactgc tctggatctt  10920
taaaagctat tggttcaggg gccaggtgta atggctcaca cctataaccc tagcactttg  10980
ggaggctgaa gcaggtggat agcctgaggt caggagtttg agacaagcct gatgaacgtg  11040
gtgaaacccc atcgctatta aaatacaaaa aattagccgg gcatggtggc aggtgcctgt  11100
aattccagct acttgggagg ctgaggcggg agaatcgctt gaacccagga ggcggaggtt  11160
gcagtgagcc aagatcgctc cactgtactc cagcctgggc gacagagcca gactctgttt  11220
caaaaaataa aatataaata aataaataaa taaataaata aataaataaa agctttaggc  11280
ttaaaggagg gtcccctgac gcagacagtg gaacaaaagc acaagcttat ggtatgactg  11340
tgggccctga ggcaggggga ggggcgggag aaccttgctg ggagggatgg gccatcaagc  11400
tgagggtcca cttctggggg cctggagggg tgaggggtgg tcgctgcagg gggtggggga  11460
aagtgactag ccctgcccaa cccctgggtc ctggctgggg tggccaggaa ggggtagcgg  11520
ggcagtgcag tgtcgggggga gagcggcttg ctgcctcgtt cttttcttgc aggccccagg  11580
atgcaggccc tggtgctact cctctgcatt ggagccctcc tcgggcacag cagctgccag  11640
aaccctgcca gccccccgga ggaggtcagt aggcaggcgg ggagggcgtg gtcagcattc  11700
cccgcccctc cttggcaggc agcacgggaa acaggacagg gaacccggac ccaggttcca  11760
ggccaggctt gggcctttat ttctctaggg ctggagtttc tccagcagca aaacagagag  11820
aaaatgtctt gccttgcctt tcaggggatg gagtagggac atgaataaga tcccaaaaga  11880
```

-continued

```
gtaaaaatct gaagcacttt taacaagtcc agggcaattc tcctgcctca gcttcccaag  11940
cagctgggat tacaggcatg caccaccaag cccggctcat tttgtatttt tagtagagac  12000
ggggtttctc catgttggtc aggctggtct cgaactcccg acctcaagtg attctcctgc  12060
ctcggcctcc caaagtgccg ggatgacagg tgtgagccac cgcacctggc caggatcttt  12120
tctcattacc ttgtcttcct agtgggggct ccactgagca ggtcatgttc ccggacattt  12180
gttcggatac tgaccaggct gtggcaggga gtgagggtat ggagtgacct ctctcctgcc  12240
cagaaagggc gcagctgggt tcccaaggca gatacaggca catggaggga agcctgggcc  12300
atatgagtgt tatggggtga gtgttggcgg aggcccaccc ttgagggaca agagcagctg  12360
ggcatcttgg cgagagccct ggactttcgt gaggtcagag tatgaattct gcgtctccct  12420
cttcctagct ttgtgaccct agacaaccct tacctcagtc tttgcttcct tgcctatgaa  12480
atgggataaa aacacccatt ctacagggcc atgtggccac tcatttattt ctcatctacc  12540
aaacacctac tcgacagggg ctggcaatgg gcggaaataa aaactcagtt ctgccgggtg  12600
cggtggctca cacctgtaat cccagcagtg tgggaggcgg agcaggacga tcccttgaat  12660
ccaggagttt gagaccagca taggcaacat agtgagaccc ctgtctctac acaaaagcaa  12720
aaattaccag gcgtggtggc aagtgcttgt ggtactacct acttgggaag ctgaggtggg  12780
aggatcactt gagcccagga gattaagact gcagtgaggg gccgggcgcg gtggctcacg  12840
cctgtaatcc cagcactttg ggaggtggag gtgggtggat cacgaggtca ggagatcgag  12900
accatcctgg ctaacacggt gaaaccccgt ctctactaaa aatacaaaaa attagctggg  12960
tgtggtgggg ggcgcctgta gtcccagcta ctcgggaggc tgaggcagga gaatggcgtg  13020
aacccgggag gtggaggttg cagtgagctg agctcgcacc actgcactcc agcctgggcg  13080
acagagtgag actccgtctc aaaaaaaaaa aaaaaaaaaa gaaagaaaga aaaactgagt  13140
tctttttttt aactttcttt ttttagagac agagtctcac tccatcaccc atgctggagt  13200
acagtggtgc gatcttggct cactgcaatc ttggcctcct gagttcaacc aattctcatg  13260
cctcagcctc ccaaatagct gggaccacag gcacgtgcca ccacgcccag ctaatttttt  13320
gggtattttt agtagagatg gggcctcacc atgttgctca ggttggtctg aaactcctga  13380
gctcaagtga tccatcttcc tcggcctgcc aaagtgctgg gattataggc ataagccact  13440
gcacctagct cccaattttt atatttatat ttatttttat ttacttattt attttttgag  13500
acagggtctc actctgtcac ccaggctgga gtacagtggc actatctcag ctcactgcaa  13560
cctctgcctc ctgggttcaa gcgaatctcg tgcctcagcc tcctgagtag ctgggattac  13620
aggcatgcac caccatgccc cgttaatttt tttgtatttt tagtagagac gggtttcacc  13680
gtgttgccca ggatggtctc gaactcctga cctcaagtga ttcacccacc tcagcctccc  13740
aaagtgctgg gattataggt gtgagccact cggctgatgg tttttaaaaa gtgggtcatg  13800
gggctgggcg cggtggctca tgcctgtaat cccagcactt tggtagaccg aggcgggtgg  13860
atcacaaggt caggagatcg agaccatcct gcctaacacg gtgaaacccc gtctctacta  13920
aaaatacaaa aaattaccca ggcatggtgg tgggcgcctg tagtcccagc tactcgggag  13980
gctgaggcag gagaatggcg tgaacctggg aggcggagct tgcagtgagc cgagatcacg  14040
ccaccgtact ccagcctgag cgacagagcg agactccgtc tcaaaaaaaa aaaaaaaaag  14100
tgggtcatag gtttcggctt ataggtcaca agtgtttaaa cctggccatg aggccaggcg  14160
cagtggcgca tgcctgtaat cccagccatt tgggaggcta aggcaggaaa atcgcttgaa  14220
ccggggaggt ggaggttgca gtgagctgag atcgcgccac tgaactctag cctgggtgac  14280
```

-continued

```
acagtaagac tctgtctcaa ataaaaaaaa aaacagctga tctctcttct gcgctgtctc  14340
tccacagaga gctcatgcgt gatcagggag taaaactcat tcccgtttta ggccaaacac  14400
agaaaaatta ggaaggacag ccccaagggg ccagaaccac caccctacac aaagccgtga  14460
ggagacagtc cctgtgcatc tctgcgagtc cctgaactca aacccaagac ttcctgtctc  14520
ctgccagggc tccccagacc ccgacagcac aggggcgctg gtggaggagg aggatccttt  14580
cttcaaagtc cccgtgaaca agctggcagc ggctgtctcc aacttcggct atgacctgta  14640
ccgggtgcga tccagcatga gccccacgac caacgtgctc ctgtctcctc tcagtgtggc  14700
cacggccctc tcggccctct cgctgggtga gtgctcagat gcaggaagcc ccaggcagac  14760
ctggagaggc cccctgtggc ctctgcgtaa acgtggctga gtttattgac atttcagttc  14820
agcgaggggt gaagtagcac caggggcctg gcctgggggt cccagctgtg taagcaggag  14880
ctcaggggct gcacacacac gattccccag ctccccgaaa ggggctgggc accactgaca  14940
tggcgcttgg cctcagggtt cgcttattga cacagtgact tcaaggcaca ttcttgcatt  15000
ccttaaccaa gctggtgcta gcctaggttc ctgggatgta actgcaaaca agcaggtgtg  15060
ggcttgccct caccgaggac acagctgggt tcacagggga actaatacca gctcactaca  15120
gaatagtctt tttttttnt tttttnnnc tttctgagac ggagtctcgc tttgtcncca  15180
aggctggagt gcagtggtgt gatctcagct cactgcaacc tctgcctccc tggttcaagg  15240
aattctcctg cctcagcctc cagagtagct gggattacag gcacctgcca tcatgcccag  15300
ctaatttttg tatttttagt agagacgggg tttcaccatg ttgcctaggc tggtctcaaa  15360
ctcccgggct caagcgatcc acccgccttg gcctcccaaa gtgctgggat tacaggcgtg  15420
agccaccgcg cctggccaga ataatcttaa gggctatgat gggagaagta cagggactgg  15480
tacctctcac tccctcactc ccaccttcca ggcctgatgc ctttaaccta cttcaggaaa  15540
atctctaagg atgaaaattc cttggccacc tagattgtct tgaagatcag cctacttggg  15600
ctctcagcag acaaaaaaga tgagtatagt gtctgtgttc tgggaggggg cttgatttgg  15660
ggccctggtg tgcagttatc aacgtccaca tccttgtctc tggcaggagc ggagcagcga  15720
acagaatcca tcattcaccg ggctctctac tatgacttga tcagcagccc agacatccat  15780
ggtacctata aggagctcct tgacacggtc actgcccccc agaagaacct caagagtgcc  15840
tcccggatcg tctttgagaa gagtgagtcg cctttgcagc ccaagttgcc tgaggcatgt  15900
gggctccatg ctgcaggctg ggggggtctt tttttttttt ggggaaagac ggagtctcgc  15960
tctgttgccc aggttggagt gaagtggcgt gatctcggtt cactgaaacc cccacctccc  16020
gggttcacac catcctcctg cctcagcctc ccgagtagct gggactgcag gngcccagct  16080
aatctttntt gtatttttag cagagacggg gtttcaccgt gtttgccagg atagtctcga  16140
tctcctgacc tggtgttctg cccgcctcga cctcccaaag tgctgggatt acaggtgtga  16200
gccaccgcgc tcggcccgtt tctaaacaat agatcatgtg tgcccaggcc tggcctggca  16260
ctggtgtgga ggaagggccc gtgagcccaa agaggctcag aaagaggaag tgggctgcag  16320
gagacggtgg gaggggcagg gagggcagtg gcgcgatgtg gggaaatctg ctgcccccct  16380
ggccagtgcc tggggatgcc agcagaagtc ctggcaagtc acaggaagat gctggctggg  16440
aagtcagggc ctgctgagcg ctaaaccaga acccgagcct ggcaggctct caaagacggg  16500
atgcttgtcg tcgagtctca tacgctaacc tctgctccgc ctcttctcag agctgcgcat  16560
aaaatccagc tttgtggcac ctctggaaaa gtcatatggg accaggccca gagtcctgac  16620
```

-continued

```
gggcaaccct cgcttggacc tgcaagagat caacaactgg gtgcaggcgc agatgaaagg  16680
gaagctcgcc aggtccacaa aggaaattcc cgatgagatc agcattctcc ttctcggtgt  16740
ggcgcacttc aagggtgagc gcgtctccaa ttctttttca tttattttac tgtattttaa  16800
ctaattaatt aattcgatgg agtcttactc tgtagcccta actggagtgc agtggtgcga  16860
tctcagctca atgcaacctc cgcctcccag gttcaagcaa ttcttgtgcc tcagcctccc  16920
gagtagctgg gattacaggg atgtaccacc actcccggct aatttttttgt atttaataga  16980
catggggttt caccatgttg gccaggctgg tctcgaactc ctgagctcag gtggtctgcc  17040
cgcctcagcc tcccaaagtg ctaggattac aagcttgagc caccacgccc agcccttttt  17100
atttttaaat taagagacaa ggtgttgcca tgatgcccag gctggtctcg aactcctggg  17160
ctcaagtaat cctcccacct tggcctccca aagtgctggg attacaggca tgagccaccg  17220
cgcccggccc ttttacattt atttatttat tttttgagac agagtcttgc tctgtcaccc  17280
aggctggagt gcagtggcgc gatctcggct cactgcaagc tctgccttcc aggttcacac  17340
cattctcctg cctcgacctc ccgagtagct gggactacag gcgcccgcca ctgcgcccta  17400
ctaatttttt gtatttttag tagagacggg gtttcaccgt ggtctcgatc tcctgacctc  17460
gtgatccacc cgcctcagcc tcccaaagtg ctgggattac aggcgtgagc cactgcgccc  17520
ggccctttta catttatttt taaattaaga gacagggtgt cactatgatg ccgaggctgg  17580
tctcgaactc ctgagctgaa gtgatcctcc cacctcggcc tcccaaaatg ctgggattac  17640
catgtccaac tttccacttc ttgtttgacc aaggatggat ggcagacatc agaaggggct  17700
tggaaaggga ggtgtcaaag accttgccca gcatggagtc tgggtcacag ctgggggagg  17760
atctgggaac tgtgcttgcc tgaagcttac ctgcttgtca tcaaatccaa ggcaaggcgt  17820
gaatgtctat agagtgagag acttgtggag acagaagagc agagagggag gaagaatgaa  17880
cactgggtct gtttggggct ttcccagctt ttgagtcaga caagatttat ttatttattt  17940
aagatggagt ctcattctgt tgcccaggct ggagtgcagt ggtgccatct tggctcacta  18000
cagcctcccc acctcccagg ttcaagtgct tctcctgcct cagcctcccg agtagttggg  18060
attacaggcg cccgccacca cacccagcta atttttgtat tttcagtaga gatggggttt  18120
cgccatgctg gccaggctgt tctcgaaaac tcctgacctc agatgatcca cccgcctcgg  18180
cctcccacag tgctgggatt acaggcgtga gccactgcgc tggccaaatc agacaaggtt  18240
taaatcccag ctctgcctgt actagctgag gaactctgca cacatttcat aacctttctg  18300
ggcctacgtt ctcaccttta acgtgaggat aatatatcta cttcatagac accttttttat  18360
gttgtctcca agttttctaa cagctctagt tctgtaccca agacatggca ggtggccaac  18420
gacatccttc taggctgtgg tgatgtgttt ggagcttgtt ccacgggtct tgtgtggggc  18480
cagccctgtt cagataaggc cttgtggggt ggcctggggt agggggaggg gttgggcaaa  18540
ctctccctta aaacgctttg taaccatctg aggcaccagc aagagcggcc cccgagcctg  18600
gacaaaatcc aaacggcttc ctacttcaag cactgatgtc tagtgagtga aggaacagct  18660
ctgggtccag gatattatag gtcacattaa actaaagggg cttggccatc agctggcttc  18720
cagagcgtca gccagttact tcacctcttt ggctttggcc tgttttcagc tacaagagga  18780
cttaatccag aggacctcag aggtccttcc cagctcagac cttctttgac tgtctcccag  18840
agacactgct gtaggagtgc acaccagttt acttttcttt cttttgtttt tgagatggag  18900
tttcgctctt tttgcctagg ctggagtgct gtggtgtgat ctcagctcac tgcaacctct  18960
ggctcccagg ttcaagtgat tctcctgtct ctgcctcccg agtagctggg attacagaca  19020
```

-continued

```
cccaccactg cacccggcta gtttttgtat tttcagtaga gatggggttt cgccatgctg  19080
gccaggctgt tctcgaaaac tcctgacctc agatgatcca tccgccttgg cctcccaaag  19140
tgctgagatt acagatgtga ggcaccacac ccggccattt ttgtattttt agtagagacg  19200
gggttttgcc atgttggcca cgctggtctc aaactcctga cctcaagtga tctgcccacc  19260
ttggcctcct gaagggctgg gactacaggc gtgagtcacc gtgcccggcc atttttgtat  19320
ttttaggaca gcgtttttttc atgttggcca ggctggtctc aaactcctga cctcaagtga  19380
tccacccacc ccggcctccc aatatgctgg gattccaggt gtgagttacc atgcccggct  19440
accactttac ttttcctgca ggctatcaca gaacgtgtac aatctagact ctaatcaacc  19500
aaatcaacgt cttgccatcg gagtttgctg gtgaagggca cttggggtcc tggaaataac  19560
tgtaggctcc aagccacaca cactgagata ggcctattcc ctgaggcctc agagcccctg  19620
acagctaagc tcccttgagt cgggcaattt tcaacaacgt gctctgggga cacagcatgg  19680
cgccactgtc tttctggtct cctggggctc agactatgtc atacacttct ttccagggca  19740
gtgggtaaca aagtttgact ccagaaagac ttccctcgag gatttctact tggatgaaga  19800
gaggaccgtg agggtcccca tgatgtcgga ccctaaggct gttttacgct atggcttgga  19860
ttcagatctc agctgcaagg tctgtgggga taggggcagg gtgggggggtg gatggaggga  19920
gaggatagag aagcaaaaca gggtagtggg aataaaatga cctttgagat ccgacagctg  19980
tctacatgtc gcctgctgtg tgactttgag caggttaata acatgtctga gctttcctcc  20040
tcttaagatg gggcagggga tcgttaccaa cacttaccct cccagggttt gttgtaagga  20100
cgaataaggt aataggaaat gggccctcag cactgggcac ccacatgttt gttctcttga  20160
gactcctatt tctagaattt aaagccaaac tttgaaaaat aatgacaaac tccaaatcgt  20220
tggcatcttt tttttttttt gagacagtct cgctctgtcg gccaggctgg agtccagtgg  20280
cacgatctcg gctcaccaca acctccgccc ccgctgggtt aaagcgattc tcttgcctca  20340
gcctcctgag tagctgggat tacaggcgtg tgcctccatg cctggctaat tttatacaga  20400
cggggtttct ccatgttggt caggctggtc tcaaactccc aaactcaggt gatccgcctg  20460
cctcggtctc ccaaaacaca ggggattcca ggcatgagcc accacgcttg gccaatcgtt  20520
ggcattctaa ggctttcagt gtacctgact tcttttagtt ctaagtctgt aactgttaac  20580
ctttcttggg ccacggctat cacacggatc tctctgggaa tctgacgaca gtgcctcaaa  20640
cccgagggag caccgccagg tgtgcacaca cgtttctgtc aacgatttcg gaggactctt  20700
gggatccctg aacaccatct gttccatggg accttaggtt aagagcctct gttcaaagga  20760
ggcttttgct cttggtgggt ggatggggtg aagtctccaa gccctcttrc ggscccttcg  20820
gtattcctat nccccggttc tgccctgtct tagtccagtg ctctctattt aacaaatgag  20880
cagtaaatgt acaccgatgg actttgggag acaataaaga cctgatattc aattctagct  20940
ccttaaacca caggagaaca ttctttcagc agacaacttc agttggtatt aggccaaggt  21000
aagaaaggcc aacagcatcc ttttctgaag aaacctcagg agatggctct ctgccagaaa  21060
gctataacct ggaaggggaa ttgtaaaata gatgaggggc tggatgaagg acgagaccag  21120
ggccccgtca cgggagaggg aaggcagctc ctggctgtgt ctgtcccccg gcttttgggc  21180
tctgaaggac taaccacatg ctttctcact tgtctcagat tgcccagctg cccttgaccg  21240
gaagcatgag tatcatcttc ttcctgcccc tgaaagtgac ccagaatttg accttgatag  21300
aggagagcct cacctccgag ttcattcatg acatagaccg agaactgaag accgtgcagg  21360
```

-continued

```
cggtcctcac tgtccccaag ctgaagctga gttacgaagg cgaagtcacc aagtccctgc  21420

aggagatgag tatgtctgaa gaccctttcg ctcttggtgg gtggatgggg tggggcaggg  21480

tctttgggcc ttccactgtg ctaagcagaa cgcaagggct ccacaggctt gtagggggc  21540

cgtggatgag tccttaatcc tcatcgtgcc agaagggaag gctgaactgc cttctctcat  21600

cagactcatt cctcagcctc acgagcagac ctccctgaca ggcgctcaca acactgcctc  21660

tcaagacgag tctgtctgac ctgttttctc atcttgacct aacttgctaa atgctcctgg  21720

gcaagtcact ccaccctcgg tcagctcaga cctcttcagg cctcagagaa agtcaacagt  21780

gctgcgccat cccagcttgc ttgcaaaggg atcccttggt tggggtgttg gggaaggcag  21840

ggttttaacg gaaatctctc tccatctcta cagagctgca atccttgttt gattcaccag  21900

actttagcaa gatcacaggc aaacccatca agctgactca aggtggaaca ccgggctggc  21960

tttgagtgga acgaggatgg ggcgggaacc acccccagcc cagggctgca gcctgcccac  22020

ctcaccttcc cgctggacta tcaccttaac cagcctttca tcttcgtact gagggacaca  22080

gacacagggg cccttctctt cattggcaag attctggacc ccaggggccc ctaatatccc  22140

agtttaatat tccaataccc tagaagaaaa cccgagggac agcagattcc acaggacacg  22200

aaggctgccc ctgtaaggtt tcaatgcata caataaaaga gctttatccc taacttctgt  22260

tacttcgttc ctcctcctat tttgagctat gcgaaatatc atatgaagag aaacagctct  22320

tgaggaattt ggtggtcctc tacttctagc ctggttttat ctaaacactg caggaagtca  22380

ccgttcataa gaactcttag ttacctgtgt tggataaggc acggacagct tctctgctct  22440

gggggtattt ctgtactagg atcagtgatc ctcccgggag ggcg                   22484
```